(12) United States Patent
Hastings et al.

(10) Patent No.: US 12,232,793 B2
(45) Date of Patent: *Feb. 25, 2025

(54) VAPOR ABLATION SYSTEMS AND METHODS

(71) Applicant: Boston Scientific Scimed, Inc., Maple Grove, MN (US)

(72) Inventors: Roger Noel Hastings, Naples, FL (US); Steven Carlson, St. Paul, MN (US); Mark Schrom, Forest Lake, MN (US); Michael Hoey, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 231 days.

This patent is subject to a terminal disclaimer.

(21) Appl. No.: 18/085,854

(22) Filed: Dec. 21, 2022

(65) Prior Publication Data

US 2023/0123218 A1 Apr. 20, 2023

Related U.S. Application Data

(63) Continuation of application No. 16/414,991, filed on May 17, 2019, now Pat. No. 11,559,345, which is a
(Continued)

(51) Int. Cl.
*A61B 18/04* (2006.01)
*A61B 17/00* (2006.01)
(Continued)

(52) U.S. Cl.
CPC .... *A61B 18/04* (2013.01); *A61B 2017/00017* (2013.01); *A61B 2017/00274* (2013.01);
(Continued)

(58) Field of Classification Search
CPC .......... A61B 18/04; A61B 2018/00636; A61B 2018/00744; A61B 2018/048; A61B 2018/00547; A61B 2018/00577
See application file for complete search history.

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| CN | 2061443 U | 9/1990 |
| CN | 2418844 Y | 2/2001 |

(Continued)

OTHER PUBLICATIONS

US 5,326,343 A, 07/1994, Rudie et al. (withdrawn)
(Continued)

*Primary Examiner* — Daniel W Fowler
(74) *Attorney, Agent, or Firm* — Bookoff McAndrews, PLLC

(57) ABSTRACT

A vapor delivery system and method is provided that is adapted for treating prostate tissue. The vapor delivery system includes a vapor delivery needle configured to deliver condensable vapor energy to tissue. In one method, the vapor delivery system is advanced transurethrally into the patient to access the prostate tissue. The vapor delivery system includes a generator unit and an inductive heating system to produce a high quality vapor for delivery to tissue. Methods of use are also provided.

20 Claims, 10 Drawing Sheets

Related U.S. Application Data continuation of application No. 15/011,005, filed on Jan. 29, 2016, now Pat. No. 10,342,593.

(60) Provisional application No. 62/109,540, filed on Jan. 29, 2015.

(51) Int. Cl.
  *A61B 18/00* (2006.01)
  *A61B 90/00* (2016.01)

(52) U.S. Cl.
  CPC .............. *A61B 2017/00398* (2013.01); *A61B 2018/00029* (2013.01); *A61B 2018/00517* (2013.01); *A61B 2018/00547* (2013.01); *A61B 2018/00577* (2013.01); *A61B 2018/00636* (2013.01); *A61B 2018/00744* (2013.01); *A61B 2018/00982* (2013.01); *A61B 2018/048* (2013.01); *A61B 2090/065* (2016.02); *A61B 2218/002* (2013.01); *A61B 2218/007* (2013.01)

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,249,585 A | 10/1993 | Turner et al. |
| 5,254,096 A | 10/1993 | Rondelet et al. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,235,022 B1 | 5/2001 | Hallock et al. |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman |
| 6,409,722 B1 | 6/2002 | Hoey et al. |
| 6,423,027 B1 | 7/2002 | Gonon |
| 6,440,127 B2 | 8/2002 | McGovern et al. |
| 6,461,296 B1 | 10/2002 | Desai |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |

(56) References Cited

U.S. PATENT DOCUMENTS

| | | |
|---|---|---|
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,827,718 B2 | 12/2004 | Hutchins et al. |
| 6,855,141 B2 | 2/2005 | Lovewell |
| 6,905,475 B2 | 2/2005 | Hauschild et al. |
| 6,887,237 B2 | 5/2005 | McGaffigan |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,740,957 B2 | 6/2014 | Masotti |
| 8,801,702 B2 | 8/2014 | Hoey et al. |
| 8,900,223 B2 | 12/2014 | Shadduck |
| 9,198,708 B2 | 12/2015 | Hoey et al. |
| 2001/0032002 A1 | 10/2001 | McClurken et al. |
| 2002/0032463 A1 | 3/2002 | Cruise et al. |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0015406 A1* | 1/2008 | Dlugos ............ A61M 5/14586<br>600/37 |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0281297 A1 | 11/2008 | Pesach et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0259271 A1 | 10/2012 | Shadduck et al. |
| 2012/0265276 A1 | 10/2012 | Curley |
| 2012/0323167 A1 | 12/2012 | Hoey et al. |
| 2013/0006231 A1 | 1/2013 | Sharma et al. |
| 2013/0066308 A1 | 3/2013 | Landman |
| 2013/0072855 A1 | 3/2013 | Sherry et al. |
| 2013/0074847 A1 | 3/2013 | Hoey et al. |
| 2013/0172867 A1 | 7/2013 | Shadduck et al. |
| 2013/0261692 A1 | 10/2013 | Cardinal et al. |
| 2014/0039356 A1 | 2/2014 | Sachs et al. |
| 2014/0081208 A1* | 3/2014 | Maloney ............ A61B 17/3478<br>604/121 |
| 2014/0200568 A1 | 7/2014 | Sharma |

(56) References Cited

U.S. PATENT DOCUMENTS

| | | |
|---|---|---|
| 2014/0276713 A1 | 9/2014 | Hoey et al. |
| 2014/0288543 A1 | 9/2014 | Hoey et al. |
| 2014/0324037 A1 | 10/2014 | Hoey |
| 2014/0354381 A1 | 12/2014 | Kohlhafer |
| 2015/0025515 A1 | 1/2015 | Hoey et al. |
| 2015/0025516 A1 | 1/2015 | Hoey et al. |
| 2015/0126990 A1 | 5/2015 | Sharma et al. |
| 2015/0157384 A1 | 6/2015 | Hoey et al. |
| 2016/0015445 A1 | 1/2016 | Hoey et al. |
| 2016/0081736 A1 | 3/2016 | Hoey et al. |
| 2017/0056089 A1 | 3/2017 | Hoey et al. |
| 2017/0196702 A1* | 7/2017 | Agarwal ............... A61F 2/4601 |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101803947 A | 8/2010 |
| JP | 7-507696 A | 8/1995 |
| JP | 8-501957 A | 3/1996 |
| JP | 8-504613 A | 5/1996 |
| JP | 11-318925 A | 11/1999 |
| JP | 200014663 A | 1/2000 |
| JP | 2000005191 A | 1/2000 |
| JP | 2001500763 A | 1/2001 |
| JP | 2005-502405 A | 1/2005 |
| JP | 2005-514085 A | 5/2005 |
| JP | 2005137916 A | 6/2005 |
| WO | 92/10142 A1 | 6/1992 |
| WO | 01/24715 A1 | 4/2001 |
| WO | 03/088851 A1 | 10/2003 |
| WO | 03/096871 A2 | 11/2003 |
| WO | 2005/102416 A1 | 11/2005 |
| WO | 2006/004482 A1 | 1/2006 |
| WO | 2008/083407 A1 | 7/2008 |
| WO | 2010/080467 A2 | 7/2010 |
| WO | 2013/160772 A2 | 10/2013 |
| WO | 2014153082 A2 | 9/2014 |
| WO | 2015/089190 A1 | 6/2015 |
| WO | 2017/106843 A1 | 6/2017 |

OTHER PUBLICATIONS

Hoey et al.; U.S. Appl. No. 15/851,333 entitled "Vapor ablation systems and methods," filed Dec. 21, 2017.

Hoey et al.; U.S. Appl. No. 15/864,957 entitled "Transperineal Vapor ablation systems and methods," filed Jan. 8, 2018.

Hoey et al.; U.S. Appl. No. 15/900,295 entitled "Systems and methods for prostate treatment," filed Feb. 20, 2018.

Hastings et al.; U.S. Appl. No. 15/035,944 entitled "Vapor ablation systems and methods," filed May 11, 2016.

Hoey et a.; U.S. Appl. No. 15/154,536 entitled "Systems and methods for treating the bladder with condensable vapor," filed May 13, 2016.

Hai; Photoselective Vaporization Prostatectomy: A Palliative Treatment Option for Men with Urinary Obstruction Secondary to Prostate Cancer; PCRI Prost. Cancer Rsrch. Inst. Reprint from PCRI Insights Nov. 2005, vol. 8(4); Dwnld from http://www.prostate-cancer.org/pcricms/node/233 on May 10, 2012; 4 pages.

Nguyen et al.; Updated results of magnetic resonance imaging guided partial prostate brachytherapy for favorable risk prostate cancer: Implications for focal therapy; J. Urol.; pp. 1151-1156; Oct. 2012.

Wang et al., "Effects of Hyperbaric Oxygen Combined With Electroacupuncture Therapy on Bladder Function in Rats After Spinal Cord Injury," Chongqing Medicine 25, Sep. 10, 2012, pp. 2577-2580.

* cited by examiner

VAPOR ABLATION SYSTEMS AND METHODS

CROSS REFERENCE TO RELATED APPLICATIONS

This application is a continuation of U.S. patent application Ser. No. 16/414,991, filed May 17, 2019, which is a continuation of U.S. patent application Ser. No. 15/011,005, filed Jan. 29, 2016, issued as U.S. Pat. No. 10,342,593, which claims the benefit of priority of U.S. Provisional Patent Application No. 62/109,540, filed Jan. 29, 2015, each of which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to devices and related methods for treatment of benign prostatic hyperplasia using a minimally invasive approach. More specifically, the present disclosure relates to treating benign prostatic hyperplasia with vapor delivered to the prostate.

BACKGROUND

Benign prostatic hyperplasia (BPH) is a common disorder in middle-aged and older men, with prevalence increasing with age. At age 50, more than one-half of men have symptomatic BPH, and by age 70, nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate early in life is the size and shape of a walnut and prior to the enlargement resulting from BPH, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

In the male urogenital anatomy, the prostate gland is located below the bladder and the bladder neck. The walls of the bladder can expand and contract to cause urine flow through the urethra, which extends from the bladder, through the prostate and penis. The portion of urethra that is surrounded by the prostate gland is referred to as the prostatic urethra. The prostate also surrounds the ejaculatory ducts which have an open termination in the prostatic urethra. During sexual arousal, sperm is transported from the testes by the ductus deferens to the prostate which provides fluids that combine with sperm to form semen during ejaculation. On each side of the prostate, the ductus deferens and seminal vesicles join to form a single tube called an ejaculatory duct. Thus, each ejaculatory duct carries the seminal vesicle secretions and sperm into the prostatic urethra.

The prostate glandular structure can be classified into three zones: the peripheral zone, transition zone, and central zone. Peripheral zone PZ comprises about 70% of the volume of a young man's prostate. This sub-capsular portion of the posterior aspect of the prostate gland surrounds the distal urethra and 70 to 80% of cancers originate in the peripheral zone tissue. The central zone CZ surrounds the ejaculatory ducts and contains about 20-25% of the prostate volume. The central zone is often the site of inflammatory processes. The transition zone TZ is the site in which benign prostatic hyperplasia develops, and contains about 5-10% of the volume of glandular elements in a normal prostate, but can constitute up to 80% of such volume in cases of BPH. The transition zone consists of two lateral prostate lobes and the periurethral gland region. There are natural barriers around the transition zone, i.e., the prostatic urethra, the anterior fibromuscular stroma, and a fibrous plane between the transition zone and peripheral zone. The anterior fibromuscular stroma or fibromuscular zone is predominantly fibromuscular tissue.

BPH is typically diagnosed when the patient seeks medical treatment complaining of bothersome urinary difficulties. The predominant symptoms of BPH are an increase in frequency and urgency of urination, and a significant decrease in the rate of flow during urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transition zone which traverses the prostatic urethra.

In early stage cases of BPH, pharmacological treatments can alleviate some of the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical or less-invasive thermal ablation device interventions. A number of methods have been developed using electrosurgical or mechanical extraction of tissue, and thermal ablation or cryoablation of intracapsular prostatic tissue. In many cases, such interventions provide only transient relief, and these treatments often cause significant peri-operative discomfort and morbidity.

In one thermal ablation method, RF energy is delivered to prostate tissue via an elongated RF needle being penetrated into a plurality of locations in a prostate lobe. The elongated RF needle is typically about 20 mm in length, together with an insulator that penetrates into the lobe. The resulting RF treatment thus ablates tissue away from the prostatic urethra and does not target tissue close to, and parallel to, the prostatic urethra. The application of RF energy typically extends for 1 to 3 minutes or longer which allows thermal diffusion of the RF energy to ablate tissue out to the capsule periphery. Such RF energy delivery methods may not create a durable effect, since smooth muscle tissue and alpha adrenergic receptors are not uniformly ablated around the prostatic urethra or within the transition zone. As a result, tissue in the prostate lobes can continue to grow and impinge on the urethra thus limiting long-term effectiveness of the treatment.

SUMMARY OF THE DISCLOSURE

A vapor delivery system is provided, comprising a generator unit including a cradle, a syringe assembly disposed in the cradle and configured to interact with the cradle to deliver a fluid at a controlled rate, an inductive heating system fluidly coupled to the syringe assembly and configured to receive fluid from the syringe assembly, a force sensor disposed in the cradle and configured contact the cradle and/or syringe assembly to generate an electrical signal proportional to a force exerted on the force sensor by the cradle and/or syringe assembly, and an electronic controller configured control delivery of fluid and RF power to the inductive heating system for the production of vapor, the electronic controller being further configured to calibrate the electrical signal as representing a fluid pressure within the syringe assembly, the electronic controller being further configured to stop delivery of fluid and/or RF power to the inductive heating system when the fluid pressure falls outside of a desired range of fluid pressures.

In some embodiments, the cradle is arranged such that a distal end of the syringe assembly is held at a higher elevation than a proximal end of the syringe assembly when the syringe assembly is inserted into the cradle.

In one embodiment, the cradle is configured to purge any air from the syringe assembly during a priming procedure in which fluid is force from the syringe assembly through the vapor delivery system.

In another embodiment, the cradle further comprises a piston coupled to a linear motor, wherein the piston interacts with a plunger of the syringe assembly to delivery fluid from the syringe assembly.

In some embodiments, a contact switch is activated when the syringe assembly is inserted into the cradle.

In one embodiment, the inductive heating system comprises an inner fluid coil surrounded by an outer conductive coil.

A method of controlling a flow of vapor is provided, comprising receiving a syringe assembly into a cradle of a generator unit, delivering a fluid at a controlled rate from the syringe assembly to an inductive heating system fluidly coupled to the syringe assembly, measuring a force exerted on a force sensor that is disposed in the cradle and configured contact the cradle and/or syringe assembly during fluid delivery, and calibrating the measured force with an electronic controller to represent a fluid pressure within the syringe assembly, and stopping delivery of fluid to the inductive heating system when the fluid pressure falls outside of a desired range of fluid pressures.

A method of treating prostate tissue is provided, comprising inserting a vapor delivery system transurethrally into a patient to access the prostatic urethra of the patient, advancing a vapor delivery needle generally transverse to the vapor delivery system through the prostatic urethra and into a transition zone of the prostate, and delivering vapor through distally facing vapor delivery ports of the vapor delivery needle to direct the vapor distally from the device into the prostate.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

In general, one method for treating BPH comprises introducing a heated vapor interstitially into the interior of a prostate, wherein the vapor controllably ablates prostate tissue. This method can utilize vapor for applied thermal energy of between 50 calories and 300 calories per each individual vapor treatment (and assumes multiple treatments for each prostate lobe) in an office-based procedure. The method can cause localized ablation of prostate tissue, and more particularly the applied thermal energy from vapor can be localized to ablate tissue adjacent the urethra without damaging prostate tissue that is not adjacent the urethra.

The present disclosure is directed to the treatment of BPH, and more particularly for ablating transitional zone prostate tissue without ablating central or peripheral zone prostate tissue. In one embodiment, the present disclosure is directed to treating a prostate using convective heating in a region adjacent the prostatic urethra. The method of ablative treatment is configured to target smooth muscle tissue, alpha adrenergic receptors, sympathetic nerve structures and vasculature parallel to the prostatic urethra between the bladder neck region and the verumontanum region to a depth of less than 2 cm.

The system can include a vapor delivery mechanism that delivers vapor media, including water vapor. The system can utilize a vapor source configured to provide vapor having a temperature of at least 60-140° C. In another embodiment, the system further comprises a computer controller configured to deliver vapor for an interval ranging from 1 second to 30 seconds.

In some embodiments, the system further comprises a source of a pharmacologic agent or other chemical agent or compound for delivery with the vapor. These agents include, without limitation, an anesthetic, an antibiotic or a toxin such as Botox®, or a chemical agent that can treat cancerous tissue cells. The agent also can be a sealant, an adhesive, a glue, a superglue or the like.

Figure 1:
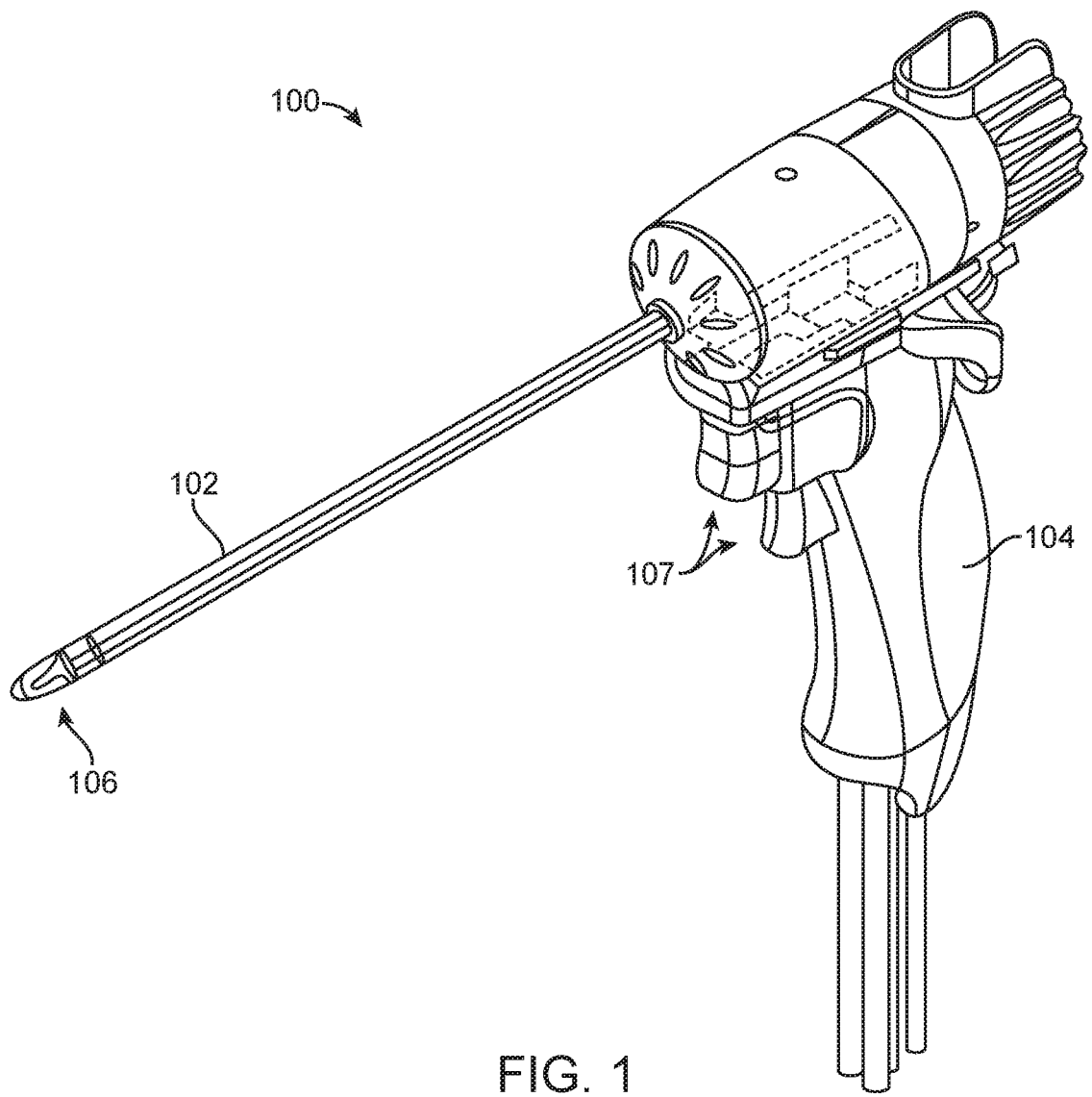
FIG. 1 shows one embodiment of a vapor delivery system.

FIG. 1 shows one embodiment of a vapor delivery system. Vapor delivery system 100 can have an elongate shaft 102 configured for insertion into the urethra of a patient and a handle portion 104 for gripping with a human hand. The vapor delivery system 100 can include a vapor delivery needle 106 disposed in the shaft that is configured to extend from a distal portion of the elongate shaft 102. The vapor delivery needle can extend generally perpendicular to or transverse from the shaft, and can include one or more vapor delivery ports configured to deliver a flow of vapor media from the needle into prostate tissue. The vapor delivery system 100 can further include one or more triggers, buttons, levers, or actuation mechanisms 107 configured to actuate the various functions of the system. For example, the actuation mechanism can be configured to extend/retract the vapor delivery needle, and start/stop the flow of vapor, aspiration, and a cooling and/or irrigation fluid such as saline.

In some embodiments, the triggers or actuation mechanisms 107 can be manipulated in such a way as to control varying degrees or flow rates of vapor and/or irrigation. In one specific embodiment, the triggers or actuation mechanisms 107 can comprise a first trigger configured to extend/retract the vapor delivery needle, a second trigger configured to start/stop the flow of vapor, and a third trigger configured to provide a cooling and/or irrigation fluid such as saline. In another embodiment, a single trigger or actuation mechanism can both extend/retract the vapor delivery needle and start/stop the flow of vapor. In one embodiment, a single press or depression of one of the triggers, such as a trigger that provides the cooling and/or irrigation fluid, may provide a standard irrigation flush, while a rapid double press or depression of the trigger may provide a "turbo" irrigation flush in which the flow rate of irrigation is increased over the standard flush flow rate. This feature may be useful, for example, if the physician encounters a blockage, needs additional cooling, or has reduced vision in the urethra and/or prostate due to accumulation of blood or other bodily fluids.

The fluid or irrigation source can provide a fluid, such as saline, through a separate lumen in the shaft to provide irrigation and flushing to tissue during insertion of the system and during vapor delivery to tissue. In some embodiments, the irrigation can be used to clear blood and debris from tissue lumens to increase visibility. The irrigation can also provide cooling to the urethra of the patient, both via direct contact of the irrigation fluid with the urethra as well as cooling the shaft of the vapor delivery system as the fluid flows from the irrigation source through the shaft and into contact with the tissue. Urethral flush can be used during the lesion formation. In one embodiment, the flush rate can be approximately 80 mL/minute, or ranging from 20 to 400 mL/minute. Changes in flush rate will change the amount of tissue cooling (depth) into the urethra and prostate, which can affect lesion size.

Figure 2A:
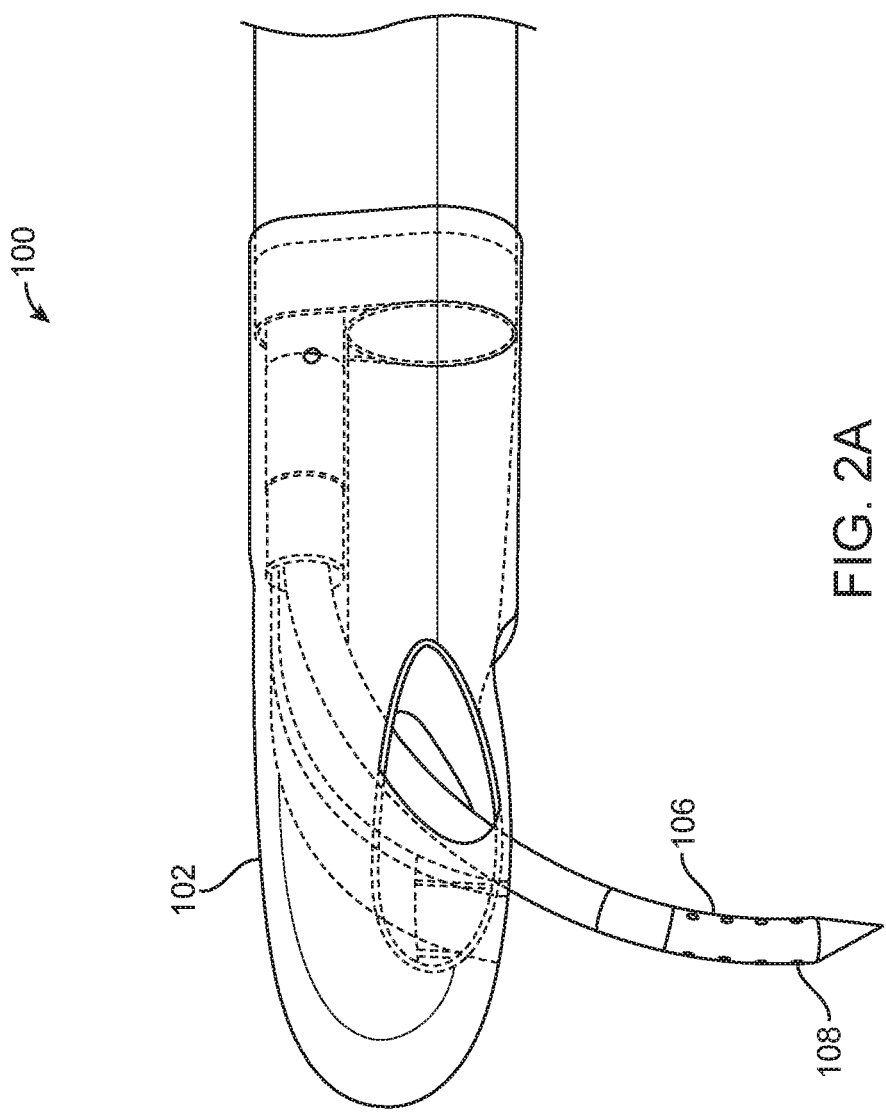
FIGS. 2A-2B show close-up views of a distal portion of the vapor delivery system including a vapor delivery needle.
Figure 2B:
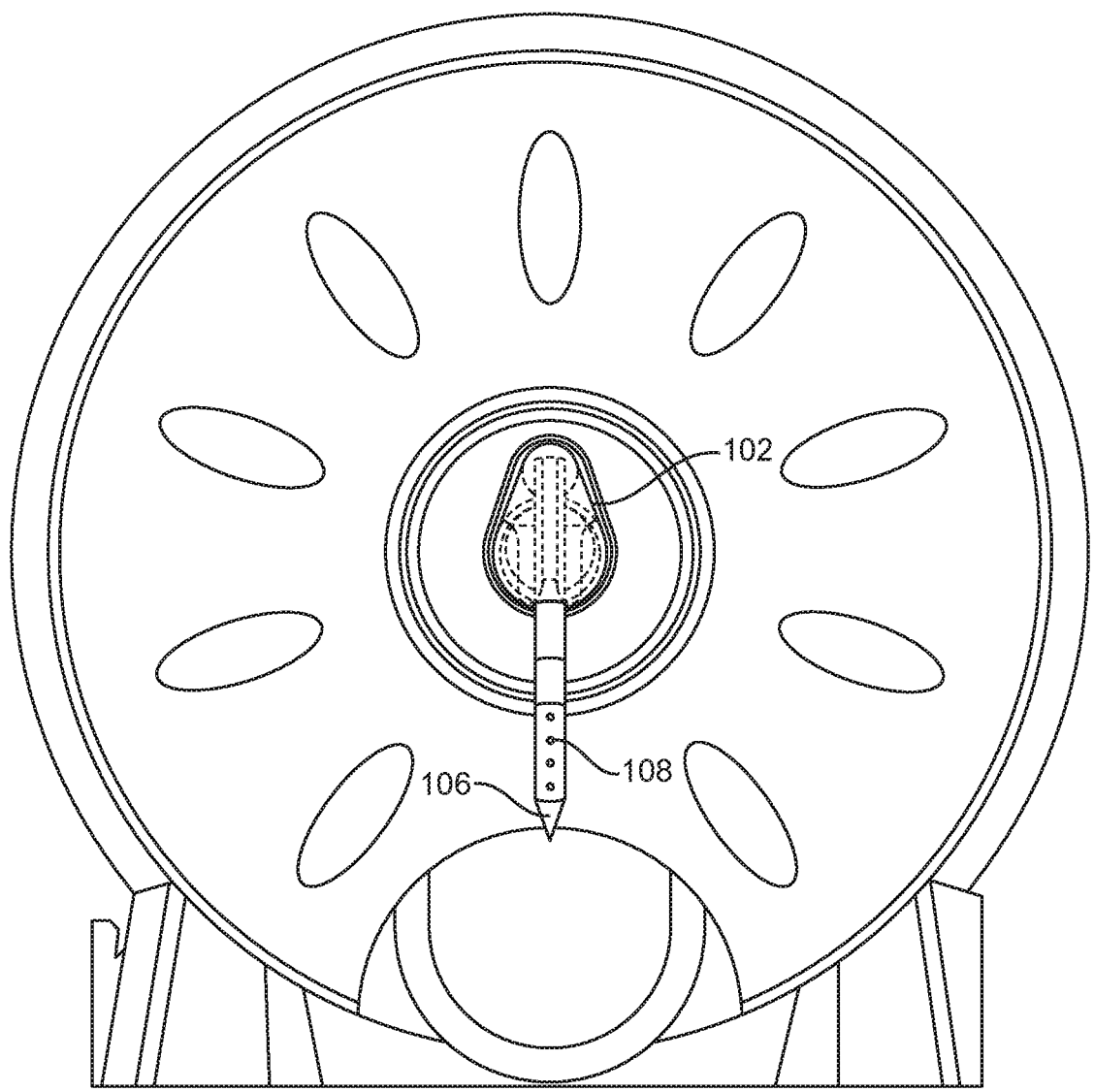

FIG. 2A shows a close-up view of the distal portion of the shaft of vapor delivery system 100, including the vapor delivery needle 106 extending beyond the shaft and exposing the vapor delivery ports 108. Vapor delivery ports 108 may be arranged in a pattern that optimizes the delivery of vapor to tissue in a given application. For example, in a system designed for treatment of BPH the delivery ports 108 comprise multiple rows of a plurality of vapor delivery ports. In one specific embodiment, the delivery ports 108 can be spaced at 120 degree intervals around the circumference of the needle, with one row of delivery ports facing distally from the front edge of the needle, as shown in FIG. 2B, to ensure ablation of tissue adjacent to the prostatic urethra. In general, the vapor delivery ports can each have a unique diameter. In one embodiment the vapor delivery ports all have the same diameter.

Figure 2C:
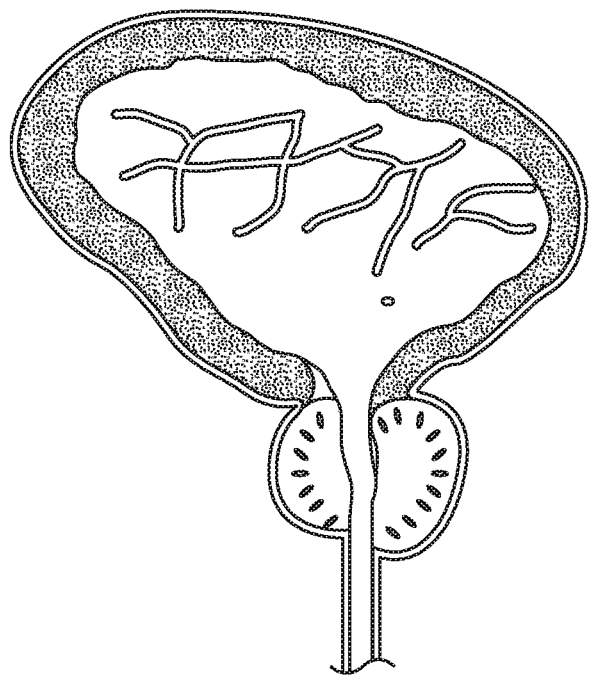
FIGS. 2C-2D show a normal prostate and an enlarged prostate being treated with a vapor delivery system.
Figure 2D:
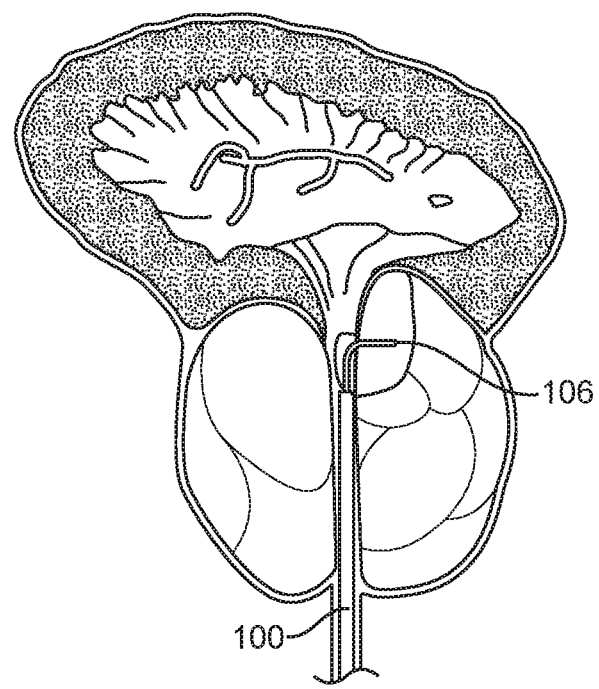

FIG. 2C shows a normal, healthy prostate, and FIG. 2D shows an enlarged prostate being treated with a vapor delivery system 100. In one embodiment, the vapor delivery system can be inserted into the urethra and advanced to the prostatic urethra through a transurethral approach. The vapor delivery needle 106 can be advanced generally transverse to the shaft of the vapor delivery system and into the prostate tissue. Vapor can be generated by the vapor delivery system and delivered into the prostate through the vapor delivery needle. As described above, the vapor delivery needle can include a row of vapor delivery ports that point distally away from the device when the vapor delivery needle is extended transverse to the shaft of the device. Referring to FIG. 2D, the vapor can be delivered to the prostate through this distally facing vapor delivery ports to ablate prostate tissue distal to the position of the vapor delivery needle in the prostate. The position of the vapor delivery needle and the vapor delivery ports can allow for ablation of transition zone tissue of the prostate extending distally from the position of the vapor delivery needle. For example, in FIG. 2D transition zone tissue is treated that extends under bladder muscular tissue that cannot be safely penetrated by a delivery device needle.

The vapor delivery system 100 can include a vapor source, an aspiration source, a fluid cooling or irrigation source, a light source, and/or an electronic controller configured to control generation and delivery of vapor from the vapor source, through a lumen of the shaft, through the vapor delivery needle, and into prostate tissue. In some embodiments, the electronic controller can be disposed on or in the vapor delivery system, and in other embodiments the electronic controller can be disposed separate from the system.

A vapor source can be provided for generating and delivering a vapor media through the vapor delivery needle to ablate tissue. In one embodiment, the vapor source can be a vapor generator that can deliver a vapor media, such as water vapor, that has a precisely controlled quality to provide a precise amount of thermal energy delivery, for example measured in calories per second. In some embodiments, the vapor source can comprise an inductive heating system disposed in the vapor delivery system (e.g., in the handle) in which a flow media is inductively heated to generate a condensable vapor such as steam.

Figure 3A:
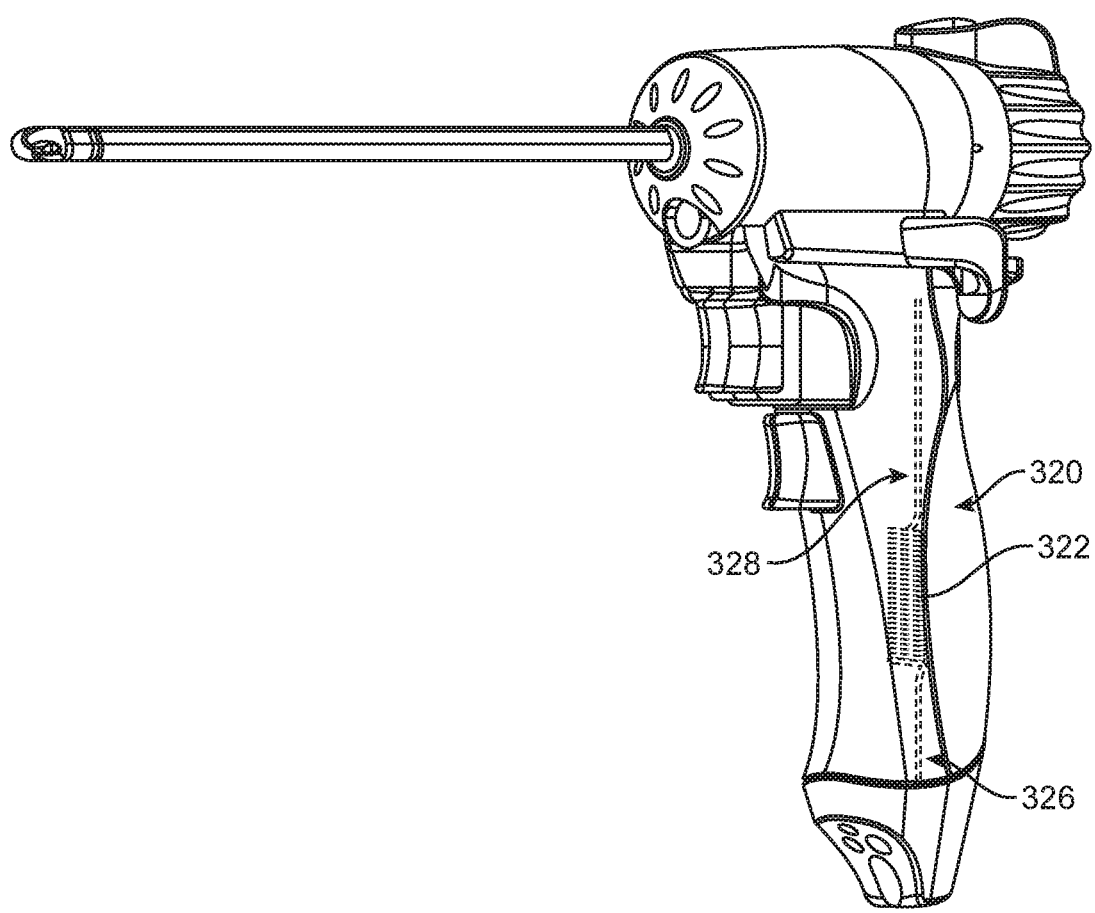
FIGS. 3A-3B show a vapor delivery system including an inductive heating system for producing high quality condensable vapor.
Figure 3B:
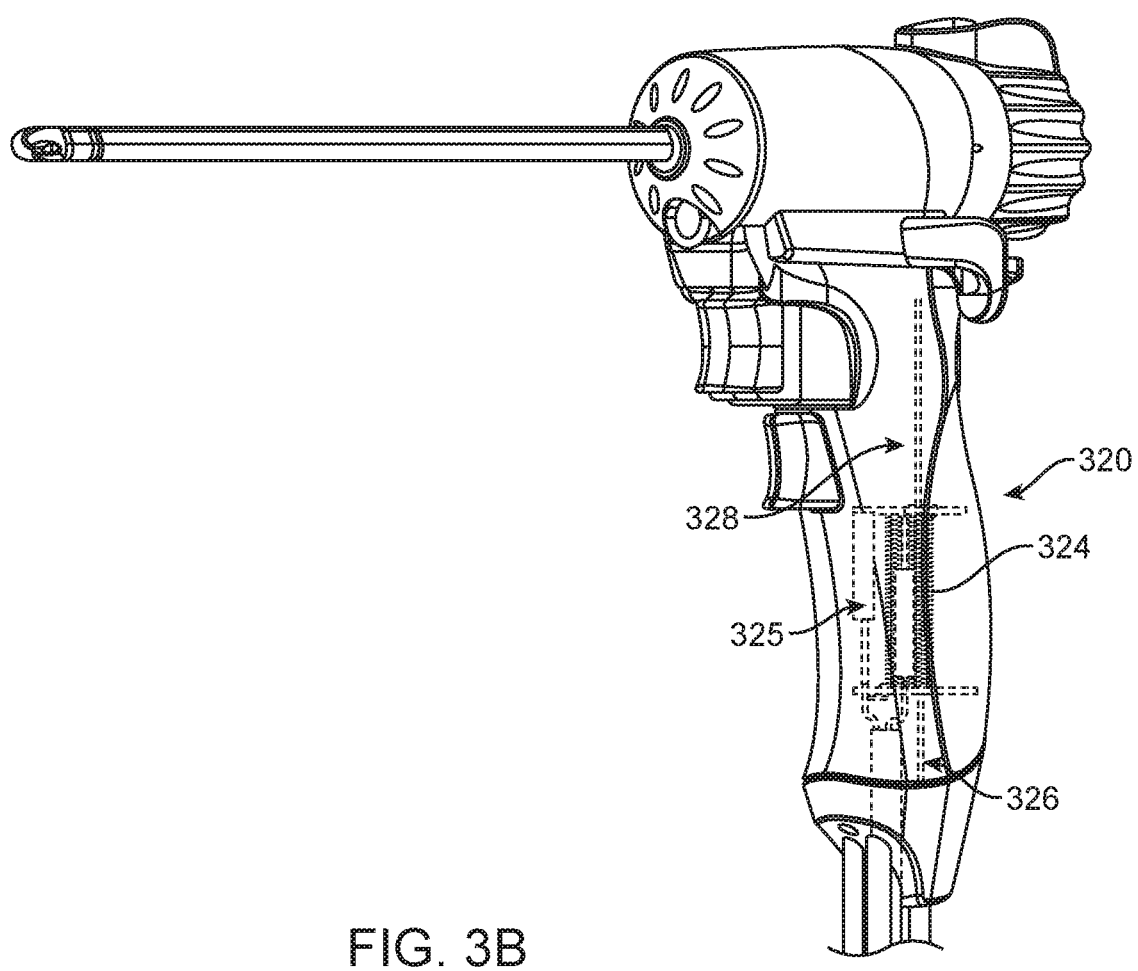

FIGS. 3A-3B illustrate one embodiment of an inductive heating system 320, comprising an inner fluid coil 322 (shown in FIG. 3A) surrounded by an outer electrically conductive coil 324 (FIG. 3B). The inner fluid coil can be constructed from steel tubing which may be annealed. The inner fluid coil may be soldered or include a solder stripe to insure electrical conductivity between coil windings. The outer conductive coil can be a conductive material, such as electrically insulated copper Litz wire having an overall diameter ranging from 18 gauge to 22 gauge. As shown, the inductive heating system 320 can be disposed within the vapor delivery system, such as within the handle. An inlet portion 326 of the inner fluid coil 322 can receive a fluid, such as sterile water, from an external fluid source. The fluid can pass through the inner fluid coil 322 as AC or RF current is applied to the outer conductive coil 324 via electrical connections 325. Current flowing in the outer conductive coil can induce currents to flow in the inner fluid coil that resistively heat the fluid within the inner fluid coil so as to produce a high quality condensable vapor, which is then delivered to the vapor delivery needle via outlet portion 328.

Figure 4:
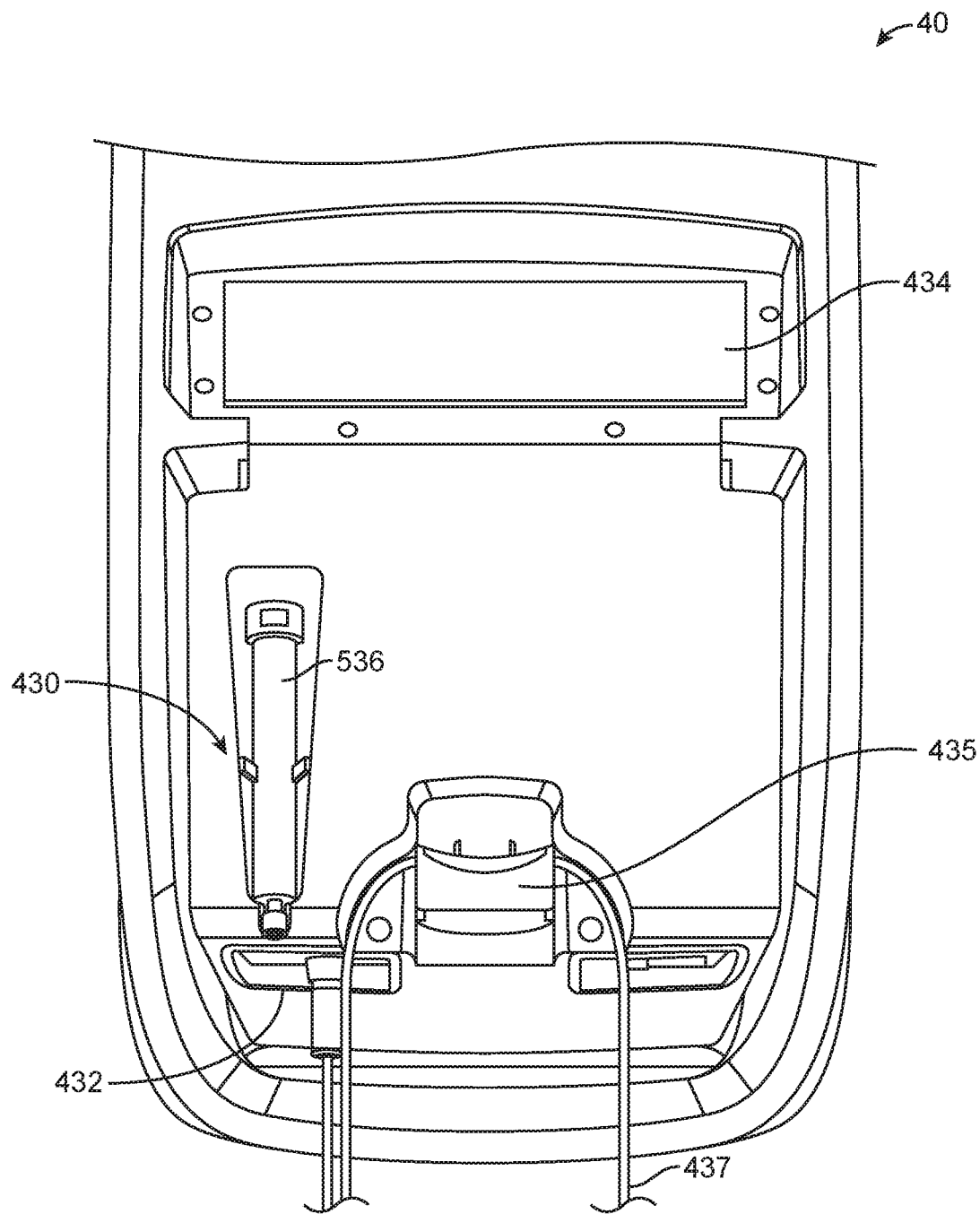
FIG. 4 shows a generator unit configured to control generation of vapor in the inductive heating system.

FIG. 4 illustrates a generator unit 40 configured to provide power and fluid to the inductive heating system for the production of vapor. The generator unit also can connect to the vapor delivery system 100 described above to provide power and other components to the system vital for operation, such as irrigation/cooling fluid, suction, etc. The generator unit can include an electronic controller and a graphical user interface (GUI) 434 to provide operating parameters and controls to the user during vapor therapy. The generator unit can include a syringe cradle 430 adapted to hold syringe assembly 536 for providing fluid, such as sterile water, to the inductive heating system.

The generator unit can also include an electrical connector 432 which can provide rf current to the inductive heating system, electrical signals to and from the switches 107 of the vapor delivery system, measurements of, for example, the temperature of the inductive heating system, and electrical signals to/from a controller of vapor delivery system, for example in its electrical connector, to identify the vapor delivery system, track its history of vapor delivery, and prevent excessive use of a given vapor delivery system. Generator unit 40 may also contain the peristaltic pump 435 that provides a flow of cooling/irrigation fluid such as saline to the vapor delivery system. In operation, flexible tubing 437 can be routed from a bag of sterile saline, through the peristaltic pump, and through tubing into the vapor delivery system. Guides or markers can be provided on the peristaltic pump 435 to insure that the tubing is inserted in a path that provides flow in a direction from the saline bag into the vapor delivery system when the pump is activated normally.

Figure 5:
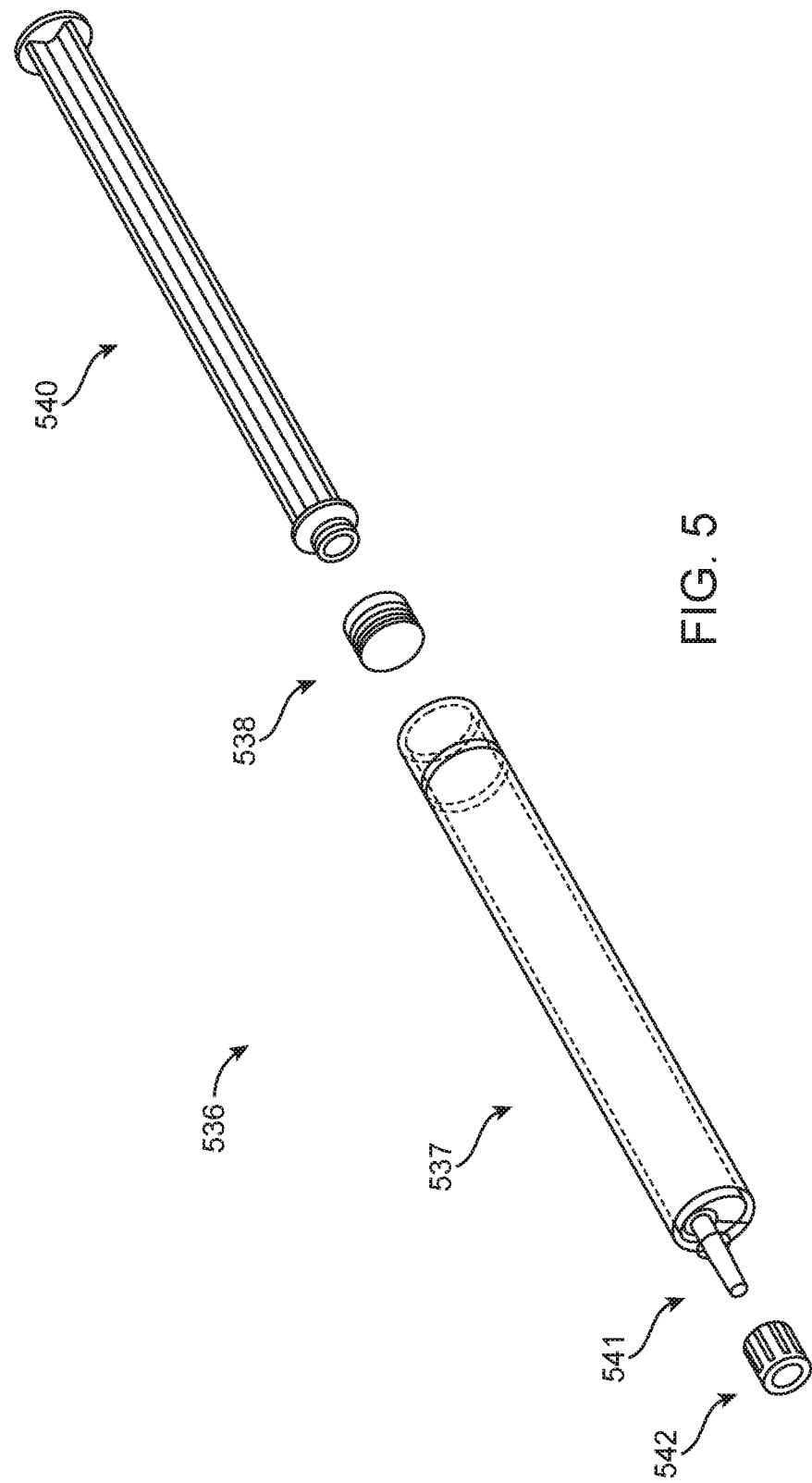
FIG. 5 shows one embodiment of a syringe assembly that interacts with the generator unit.

FIG. 5 shows syringe assembly 536 that provides a precise amount of fluid such as sterile water to the vapor delivery system 100 for conversion into vapor. Syringe assembly 536 includes a syringe 537 having exit port 541 that is offset from the center line of the syringe, with luer fitting 542 that connects to sterile water tubing on the vapor delivery system, plunger 538 that moves forward in the syringe to eject water, and backward in the syringe to fill the syringe with water, and accessory rod 540 that removably attaches to plunger 538 during system set-up to fill syringe 537. When syringe 537 has been filled with fluid, accessary rod 540 is discarded, and filled syringe 537 is inserted into the cradle of the generator unit.

Figure 6:
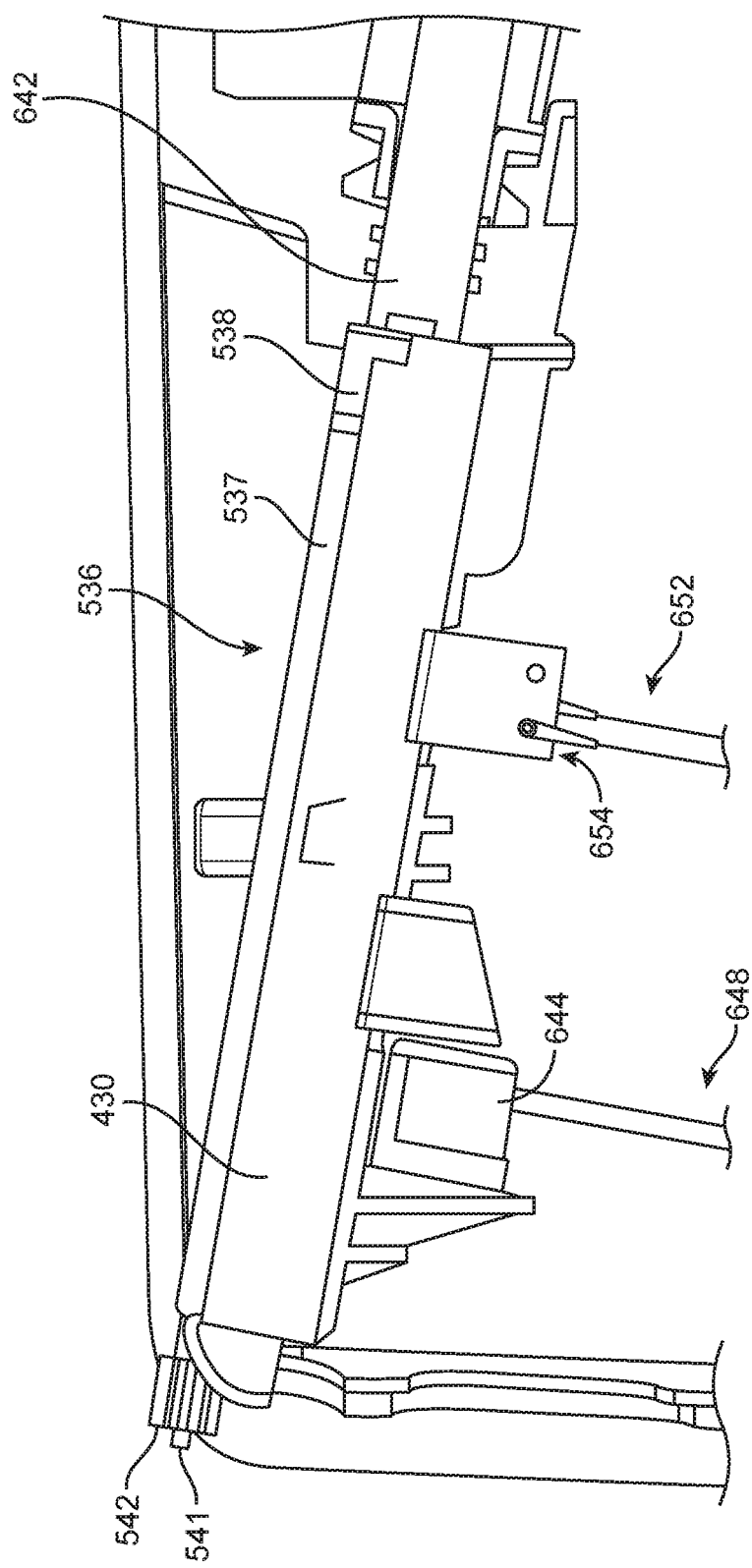
FIG. 6 shows a cross-sectional view of a syringe cradle and syringe assembly of the generator unit.

FIG. 6 shows a cross-sectional view of the syringe cradle 430 of FIG. 4, with the syringe assembly 536 of FIG. 5 inserted into cradle 430. A contact switch 654 is activated when syringe 537 is inserted into cradle 430 to insure that the syringe is in place before power is delivered to the vapor delivery system. The state of the contact switch is sensed through electrical leads 652. A force sensor 644 is disposed in the cradle such that it contacts and interacts with the cradle and/or syringe assembly 537. When the electronic controller is commanded to deliver sterile water to the vapor delivery system, piston 642 of the cradle engages syringe plunger 538, and a linear motor attached to piston 642 delivers sterile water at a precisely controlled rate from syringe 537 out through luer fitting 542 into fluid tubing connected to the inductive heating system. As sterile water is pushed, syringe 537 impinges on cradle 430, which is free to move laterally within generator 40. Forward movement of cradle 430 is prevented as it impinges upon force sensor 644. Microscopic lateral movement of force sensor 644 is translated into an electrical signal that is proportional to the force exerted on force sensor 644 by cradle 430. The electrical signal is conducted through leads 648 to the electronic controller and calibrated as the water pressure within syringe 537 and throughout the fluid tubing including within the inner coil of the inductive heating system. Water pressure is monitored by the electronic controller of the generator unit 40, and the electronic controller can be configured to stop delivery of RF power and fluid to the inductive heating system if the fluid pressure falls outside of a desired range of pressures, e.g., if the fluid pressure is too low (for example due to a leak in the water line), or too high (for example due to a blockage in the water line).

Cradle 430 is configured to purge any air from the fluid tubing during a priming procedure in which water is forced from the syringe and fills and flushes the system water and vapor lines, exiting from the vapor delivery ports of the vapor delivery device. As shown in FIG. 6, cradle 430 is designed so as to keep the distal end of syringe 537 at a higher elevation than its proximal end when inserted into the cradle, and to keep offset exit port 541 of the syringe at the top of the syringe. This design forces any air in the syringe to move under the influence of gravity to the upper distal end of the syringe and to exit the syringe to be purged from the fluid tubing during the priming procedure. Removal of air from the fluid tubing prevents over heating of the inductive heating system, and prevents loss of water volume and therefore loss of calories delivered to tissue.

The electronic controller of the generator unit can be set to control the various parameters of vapor delivery, for example, the controller can be set to deliver vapor media for a selected treatment interval at a selected flow rate, a selected pressure, or selected vapor quality. Further details on the vapor delivery system, the vapor generator, and how vapor and fluid are delivered to tissue can be found in U.S. Pat. No. 8,273,079 and PCT Publication No. WO 2013/040209, both of which are incorporated by reference. In some embodiments, the electronic controller can also control the aspiration and/or cooling irrigation functions of the vapor delivery system.

Figure 7:
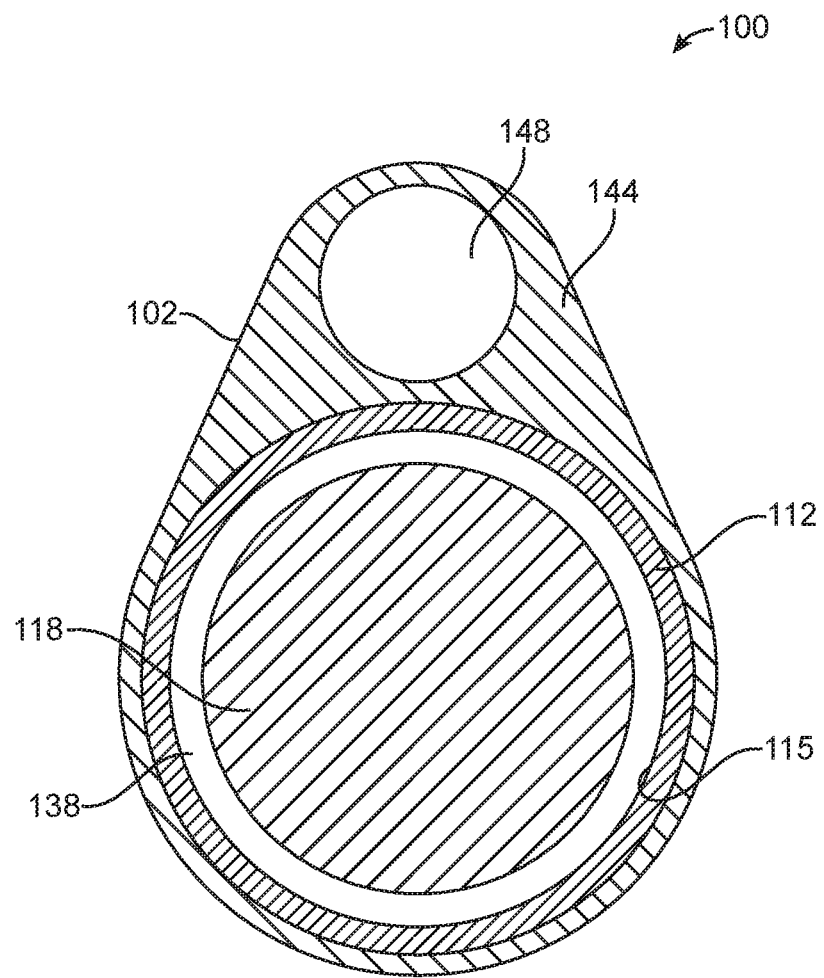
FIG. 7 is a cross-sectional view of a shaft of the vapor delivery system.

FIG. 7 provides a cross sectional view of elongate shaft 102 of vapor delivery system 100 from FIGS. 1-2. Lumen 148 can be configured to accommodate the vapor delivery needle described above and in FIGS. 1-2, to allow for the vapor delivery needle to be advanced from the shaft during vapor delivery. Lumen 115 formed within tube 112 can have a diameter ranging from about 2 to 5 mm for accommodating various endoscopes 118, while at the same time providing an annular space 138 for allowing an irrigation fluid to flow within lumen 115 and outwardly from the shaft into the distal urethra and bladder. The lumen 115 can be sized to accommodate an endoscope or camera to provide additional viewing and feedback to the physician. This endoscope or camera can provide a view of the distal end of the shaft, including a view of the vapor delivery needle when deployed. As can be seen in FIG. 7, the lumen 115 is dimensioned to provide a space 138 for fluid irrigation flow around the endoscope 118. In some embodiments, the annular space 138 can be a separate concentric lumen around the endoscope for irrigation fluid flow. The annular space 138 allows for flow of irrigation fluid from the vapor delivery system into tissue, and also provides cooling to the shaft when vapor is delivered from the vapor delivery needle (disposed in lumen 148) into tissue. Material 144 in FIG. 7 can conduct heat from the vapor delivery needle to the irrigation/cooling fluid flowing in annular space 138, or alternatively, can conduct cooling from the irrigation/cooling fluid to the vapor delivery needle, to prevent overheating of the patient (particularly the urethra) during vapor therapy.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A vapor delivery system, comprising:
   a generator unit;
   a cradle disposed in the generator unit;
   a syringe disposed in the cradle;
   a force sensor disposed in the generator unit and configured to contact the cradle and/or the syringe, wherein the force sensor is configured to generate an electrical signal indicative of a force exerted on the force sensor by the cradle and/or the syringe; and
   an electronic controller configured to receive the electrical signal, wherein the electronic controller is configured to calibrate the electrical signal to represent a pressure of fluid within the syringe.

2. The vapor delivery system of claim 1, wherein the force sensor is disposed to directly contact the cradle and/or the syringe.

3. The vapor delivery system of claim 1, wherein the electronic controller is further configured to stop delivery of the fluid if the pressure is outside of a predetermined range of fluid pressures.

4. The vapor delivery system of claim 1, wherein the cradle is arranged such that a distal end of the syringe is held at a higher elevation than a proximal end of the syringe.

5. The vapor delivery system of claim 1, wherein the cradle further comprises a piston coupled to a linear motor, and wherein the piston interacts with a plunger of the syringe to deliver fluid from the syringe.

6. The vapor delivery system of claim 1, wherein a contact switch is activated when the syringe is inserted into the cradle.

7. A vapor delivery system, comprising:
   a generator unit;
   a cradle disposed in the generator unit;
   a syringe disposed in the cradle;
   a force sensor disposed between the cradle and the generator unit or between the syringe and the cradle, wherein the force sensor is configured to generate an electrical signal indicative of a force exerted on the force sensor by the cradle; and
   an electronic controller configured to receive the electrical signal, wherein the electronic controller is configured to calibrate the electrical signal to represent a pressure of fluid within the syringe.

8. The vapor delivery system of claim 7, wherein the electronic controller is further configured to stop delivery of the fluid if the pressure is outside of a predetermined range of fluid pressures.

9. The vapor delivery system of claim 7, wherein at least a portion of the cradle is free to move in a lateral direction perpendicular to a longitudinal axis of the syringe, and wherein the force exerted is a lateral force.

10. The vapor delivery system of claim 7, wherein the cradle further comprises a piston coupled to a linear motor, wherein the piston is configured to interact with a plunger of the syringe to deliver fluid from the syringe.

11. The vapor delivery system of claim 10, wherein the interaction of the plunger and the syringe causes the force to be exerted on the force sensor by the cradle.

12. The vapor delivery system of claim 7, wherein the cradle is arranged such that a distal end of the syringe is located at a higher elevation than a proximal end of the syringe.

13. The vapor delivery system of claim 7, wherein a barrel of the syringe directly contacts the cradle.

14. A vapor delivery system, comprising:
   a generator unit;
   a cradle disposed in the generator unit;
   a syringe disposed in the cradle;
   a force sensor disposed in the generator unit and configured to generate an electrical signal indicative of a lateral force exerted on the force sensor by the cradle and/or the syringe in a lateral direction, wherein the lateral direction is a direction perpendicular to a longitudinal axis of the syringe; and
   an electronic controller configured to receive the electrical signal, wherein the electronic controller is further configured to calibrate the electrical signal to represent a pressure of fluid within the syringe.

15. The vapor delivery system of claim 14, wherein the electronic controller is further configured to stop delivery of the fluid if the pressure falls outside of a predetermined range of fluid pressures.

16. The vapor delivery system of claim 14, wherein at least a portion of the cradle is free to move laterally within the generator unit.

17. The vapor delivery system of claim 14, wherein the cradle further comprises a piston coupled to a linear motor, wherein the piston is configured to interact with a plunger of the syringe to deliver fluid from the syringe.

18. The vapor delivery system of claim 17, wherein the interaction of the plunger and the syringe causes the lateral force to be exerted on the force sensor by the cradle.

19. The vapor delivery system of claim 14, wherein the cradle is arranged such that a distal end of the syringe is located at a higher elevation than a proximal end of the syringe.

20. The vapor delivery system of claim 14, wherein a barrel of the syringe directly contacts the cradle.

* * * * *